United States Patent [19]

Girijavallabhan et al.

[11] Patent Number: 4,614,738
[45] Date of Patent: Sep. 30, 1986

[54] 2-(N-HETEROCYCLOALIPHATICTHIO)-PENEMS

[75] Inventors: Viyyoor M. Girijavallabhan, Parsippany; Ashit K. Ganguly, Upper Montclair; Patrick A. Pinto, Mine Hill; Richard W. Versace, Ringwood, all of N.J.

[73] Assignee: Schering Corporation, Kenilworth, N.J.

[21] Appl. No.: 478,620

[22] Filed: Mar. 25, 1983

[51] Int. Cl.$^4$ ............... C07D 499/00; A61K 31/425
[52] U.S. Cl. .................................. 514/194; 514/195; 540/310; 540/357; 540/360; 540/201
[58] Field of Search ............... 260/245.2 R; 424/270; 514/194, 195

[56] References Cited

U.S. PATENT DOCUMENTS 4,301,074 11/1981 Christensen et al. ........ 260/245.2 R
4,423,055 12/1983 McCombie ........................ 424/270
4,435,412 3/1984 Girijavallabhan et al. ... 260/245.2 R
4,559,333 12/1985 Girijavallabhan et al. ... 260/245.2 R

FOREIGN PATENT DOCUMENTS 57-176988 10/1982 Japan .

Primary Examiner—Nicholas S. Rizzo
Attorney, Agent, or Firm—Anita W. Magatti; Stephen I. Miller; Gerald S. Rosen

[57] ABSTRACT

This invention relates to 2-(N-heterocycloaliphaticthio)penems wherein the nitrogen of the heterocyclic ring is connected to the alkyl group, and to their use as antibacterial agents.

27 Claims, No Drawings

2-(N-HETEROCYCLOALIPHATICTHIO)PENEMS

BACKGROUND OF THE INVENTION

This invention relates to 2-(N-heterocycloaliphaticthio)penems and their pharmaceutically acceptable salts and esters, which compounds possess potent anti-bacterial activity.

There is a continuing need for new antibacterial agents because continued extensive use of effective anti-bacterials gives rise to resistant strains of pathogens.

SUMMARY OF THE INVENTION

This invention relates to novel 2-(N-heterocycloaliphaticthio)penems wherein a nitrogen of the aliphaticheterocyclic ring is connected to the alkyl group, and to their use as antibacterial agents. More particularly, this invention relates to 6-(1-hydroxyethyl)-2-(N-heterocycloaliphaticthio)penem-3-carboxylic acids represented by the formula

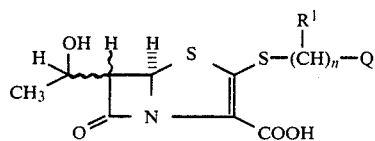

A wherein
Q is selected from the group consisting of

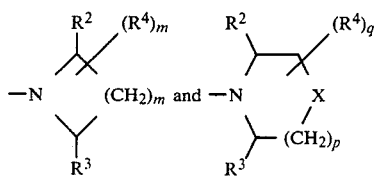

$R^1$ is hydrogen, lower alkyl, carboxy, carbamyl, cyano, hydroxy, amino, lower alkylthio, fluoro, lower alkoxy, or lower alkanoyloxy, provided that when $R^1$ is attached to a carbon atom adjacent to S or N, $R^1$ is not hydroxy, amino, lower alkylthio, fluoro, lower alkoxy, or lower alkanoyloxy;

$R^3$ and $R^3$ are independently selected from hydrogen, lower alkyl, amino(lower)alkyl, mono- and di-(lower)alkylamino(lower)alkyl, carboxy(lower)alkyl, carboxy, hydroxy(lower)alkyl, cyano, oxo, carbamyl, and mono- or di(lower)alkylcarbamyl;

$R^4$ is $R^2$, sulfo(lower)alkyl, hydroxy, amino, mono- and di-(lower)alkylamino, (lower)alkylsulfonate, sulfamyl, halogeno, hydroxylimino, or lower alkoxyimino;

X is O, S, $SO_2$, NH, $NR^2$ or $NCOR^2$;
m and n are 1 to 4;
p is 1 or 2;
q is 1 to 3; and
the pharmaceutically acceptable salts and esters thereof, in racemic or optically active form.

Preferred are compounds of formula A wherein n is 2 to 4; more preferred are those compounds wherein n is 2.

Also preferred are compounds wherein m is 2 to 3, and another group of preferred compounds is that wherein p is 1.

Preferred $R^2$ and $R^3$ substituents are hydrogen and oxo.

Preferred $R^4$ substituents are amino, hydroxy, oxo and carboxy.

The term "lower alkyl" as used herein means alkyl groups of 1 to 6 carbon atoms and includes methyl, ethyl, propyl, butyl, pentyl and hexyl and the corresponding branched chain isomers thereof. Similarly, "lower alkoxyl" means straight or branched alkoxy groups having 1 to 6 carbon atoms, e.g., methoxy, ethoxy, propoxy, butoxy, isopropoxy, and neopentoxy, and "lower alkanoyloxy" means straight or branched chain alkanoyloxy groups of 1 to 6 carbon atoms, e.g. acetoxy, propionoxy, butyryloxy, isopropionoxy and isobutyryloxy.

The term "oxo" as used herein refers to a doubly bonded oxygen atom (=O), which together with the carbon to which it is attached, forms a carbonyl group.

Compounds of the present invention possess 3 or more asymmetric carbon atoms, indicated in the partial formula B below as the 5, 6, 8 and 2' to 5'-position carbon atoms.

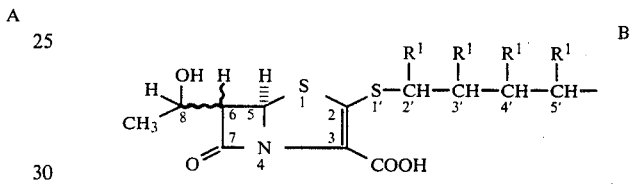

B

At the 5, 6, and 8 positions, compounds of the invention may possess 5R,6S,8R or 5R,6R,8S absolute configuration at those chiral atoms. The preferred absolute configuration for the compounds of the present invention at those positions is 5R,6S,8R.

Compounds of formula A wherein $R^1$ is other than hydrogen will have additional asymmetric carbon atom(s) as shown in formula B at the 2' to 5' positions. All the possible resulting steroisomers are included herein.

DETAILED DESCRIPTION

When tested in standardized microbiological assays, the compounds of this invention are active against such gram-positive organisms as [Staphylococcus epidermis and *Bacillus subtilis*, and such gram-negative organisms as *E. coli* and Salmonella, at test levels of 0.03 to 1.0 micrograms/ml. Additionally, they show activity against organisms which produce beta-lactamases, e.g., penicillinase and cephalosporinase, indicating a stability toward these enzymes. For instance, 5R,6S,8R-2-[2-(N-piperazinyl)ethylthio]-6-(1-hydroxyethyl)penem-3-carboxylic acid is active against *Staphylococcus aureus* 76010501 at a test level of 0.031 microgram/ml. When tested against *E. coli* 71120101 TEM-1 (a beta-lactamase producing organism) the compound exhibits activity at 0.500 microgram/ml.

The compounds of this invention and their metabolites have little or no unpleasant odor.

As antibacterial agents, the compounds of this invention are conventionally formulated for oral, parenteral, topical and transdermal use. Thus, this invention includes within its scope pharmaceutical compositions comprising the compounds of this invention in admixture with a pharmaceutically acceptable carrier therefor. In addition, the present invention also provides a method of treating bacterial infections in animals, particularly warm-blooded animals having a susceptible bacterial infection which comprises administering to said animal an antibacterial effective amount of a compound of this invention, or a pharmaceutical composition thereof. In the foregoing compositions, the compounds of this invention can be used as the sole active antibacterial agent or in combination with other antibacterial agents and/or enzyme inhibitors.

For oral administration, the compounds of this invention are typically formulated in the form of tablets, capsules, elixirs, or the like. For parenteral administration, they may be formulated into solutions or suspensions. Typical topical formulations are those such as lotions, creams, ointments, sprays, and mechanical delivery devices, e.g., transdermal. Parenteral administration is preferred. Typical pharmaceutically acceptable carriers for use in the formulations described above are exemplified by: sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinyl pyrrolidone; polyvinyl alcohol; stearic acid; alkaline earth metal stearates such as magnesium stearate; vegetable oils such as peanut oil, cottonseed oil, sesame oil, olive oil and corn oil; nonionic, cationic and anionic surfactants; ethylene glycol polymers; betacyclodextrin; fatty alcohols; hydrolyzed cereal solids; water; polyalkylene glycols; gums; and petrolatum; as well as other non-toxic compatible fillers, binders, disintegrants and lubricants commonly used in pharmaceutical formulations. The compositions may also contain preservatives, aerosol propellants and coloring, thickening, suspending, dispensing, emulsifying, wetting, stabilizing and buffering agents.

The dosage of the compounds of this invention which is administered is dependent, in the judgement of the attending clinician, upon a variety of factors, i.e., the age and weight of the individual being treated, the mode of administration, and the type and severity of the bacterial infection being prevented or reduced. Typically, the dosage administered per day will be in the range of from about 1 to 250 mg/kg and preferably from about 5 to 20 mg/kg in divided dosages. Typically, the dosage will be administered in dosage units containing convenient amounts, for example, 125, 250 or 500 mg of active ingredient combined with a suitable physiologically acceptable carrier or diluent.

As used herein, "pharmaceutically acceptable salts" means alkali metal salts such as sodium and potassium salts; alkaline earth metal salts such as calcium, magnesium and aluminum salts; amine salts formed from a wide variety of suitable organic amies, i.e., aliphatic, cycloaliphatic, (cycloaliphatic)aliphatic or araliphatic primary, secondary or tertiary mono-, di- or polyamines, or heterocyclic bases, e.g., salts derived from triethylamine, 2-hydroxyethylamine, di-(2-hydroxyethyl)amine, tri-(2-hydroxyethyl)amine, 4-aminobenzoic acid-2-diethylaminoethyl ester, 1-ethylpiperidine, bicyclohexylamine, N,N'-dibenzylethylenediamine, pyridine, collidine, quinoline, procaine, dibenzylamine, 1-ephenamine and N-alkylpiperidine. Acid addition salts formed from mineral acids such as hydrochloric, hydrobromic, hydroiodic, phosphoric or sulfuric acids, or formed from organic carboxylic or sulfonic acids such as trifluoroacetic, para-toluene sulfonic, maleic, acetic, citric, oxalic, succinic, benzoic, tartaric, fumaric, mandelic, ascorbic and malic acids. The compounds of this invention contain a 3-carboxylic group and a basic group (the heterocyclic group) which form an inner salt, i.e., a Zwitterion.

"Pharmaceutically acceptable esters" means physiologically cleavable esters, i.e., metabolizable esters known in the penicillin, cephalosporin and penem arts to be easily cleaved within the body to the parent acid. Examples of such esters are indanyl, phthalidyl, methoxymethyl, glycyloxymethyl, phenylglycyloxymethyl, thienylglycyloxymethyl, acetoxymethyl and pivaloyloxymethyl.

Preparation of the foregoing salts and esters may be carried out according to conventional procedures for forming salts of beta-lactams such as penicillins, cephalosporins and penems. For example, salts of the compound can be formed, for example, by treating with metal compounds such as alkali metal salts of suitable carboxylic acids, or with ammonia or a suitable organic amine, wherein preferably stoichiometric amounts or only a small-excess of the salt-forming agent used. Acid addition salts of the compound are obtained in the usual manner, for example, by treating with an acid or a suitable anion exchange present. Inner salts of the compounds of formula, i.e., a zwitterion, may be formed by neutralizing salts such as acid addition salts to the isoelectric point. The esters are preparable in a manner analogous to the preparation of the corresponding esters of penicillins and cephalosporins.

Salts may be converted in the usual manner into the free carboxy compounds.

The compounds of this invention are prepared by the processes disclosed in U.S. patent application Ser. No. 445,295, filed Nov. 29, 1982. The process disclosed therein referred to as process C is preferred for preparing the compounds of this invention. The process comprises:

(a) reacting an azetidinone of the formula

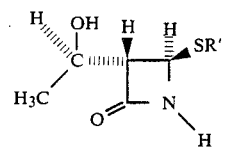

wherein R' is a sulfur protecting group selected from triphenylmethyl, 2-pyranyl, or lower alkyl carbonyl; with an α-substituted allyl acetate of formula II

WCH$_2$CO$_2$CH$_2$CH=CH$_2$,  II wherein W is a leaving group; to form the intermediate of formula III

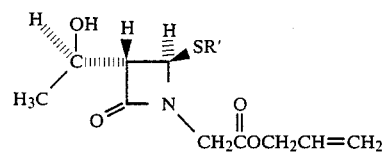

(b) treating the compound of formula III with a reactive silver, copper or mercury salt to form the compound of formula IV

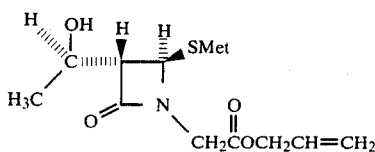

wherein Met is silver, copper or mercury.

(c) treating the compound of formula IV with a hydroxy protecting group to form the compound of formula V

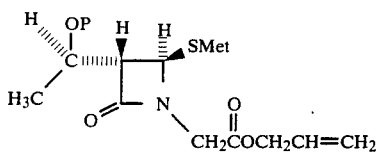

wherein P is a removable hydroxy protecting group and Met is as hereinabove defined;

(d) reacting the compound of formula V with a thiocarbonyl compound of formula VI

 S=C(—Y)$_2$   VI wherein Y is a leaving group to form a compound of formula VII

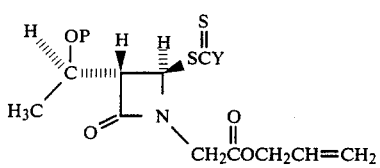

wherein Y and P are as hereinabove defined;

(e) treating compound VII with a non-nucleophilic strong base to form a compound of formula VIII(a) which is tautomeric with formula VIII(b)

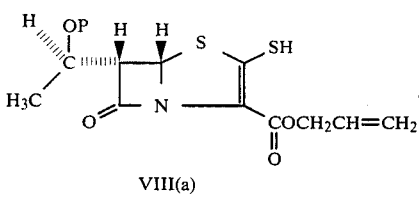 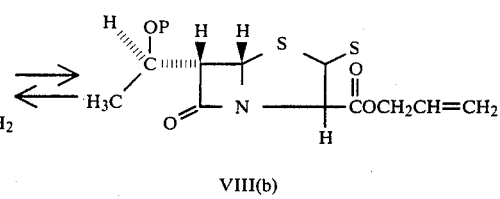

VIII(a)   VIII(b)

wherein P is as hereinabove defined;

(f) treating the compounds of formulas VIII(a) and VIII(b) under conditions which effect removal of the hydroxy protecting group to form the compounds of formula IX(a) and IX(b).

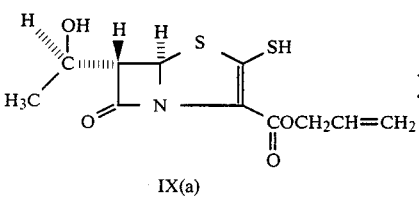 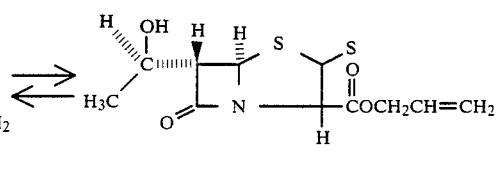

IX(a)   IX(b)

(g) reaction of the compound of formulas IX(a) and IX(b) with either a compound of the formula X

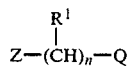

wherein Q, R$^1$ and n are as defined hereinabove and Z is a leaving group or with a compound of the formula XI

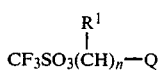

wherein Q, R$^1$ and n are hereinabove defined to form a compound of formula XII

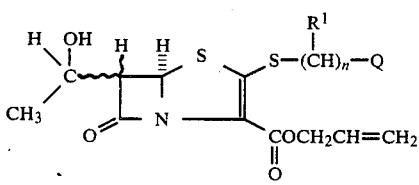

wherein Q, R$^1$ and n are defined above.

(h) treatment of a compound of formula XII under catalytic conditions to remove the allyl protecting group in the presence of an alkali base (if the product is a zwitterion, deprotection requires only the catalyst and any mild nucleophile, e.g., H$_2$O, alcohol, etc.) to form the compounds of formula A

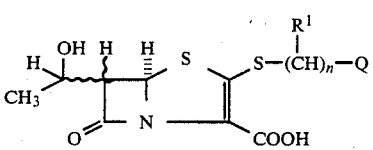

wherein X, R$^1$ and n are as hereinabove defined.

In a preferred embodiment the α-substituted allyl acetate of formula II is added to the azetidinone of formula I to form the intermediate of formula III. The intermediate of formula III is then utilized directly in steps (b), (c) and (d) which are conducted sequentially without isolation of any intermediates.

Likewise steps (e) and (f) are preferably conducted sequentially without the necessity of isolating any intermediates.

Step (a) involves the reaction of an azetidinone of formula I at 15°–30° C. in the presence of an acid acceptor with an α-substituted allyl acetate of formula II to form the compound of formula III. Preferred W leaving groups in the compound of formula II include tosyl, mesyl, chloro, bromo, iodo, and trifluoromethansulfonyl. Particularly preferred W leaving groups are iodo and bromo.

Where the solvent utilized is also an acid acceptor, for instance, pyridine, no additional reagent is utilized. Alternatively, an organic solvent such as acetonitrile may be employed. In these cases, a separate acid acceptor, organic or inorganic must be added to the system. Preferably, the reaction is conducted in acetonitrile employing cesium carbonate or tetra alkyl ammonium hydroxide as the acid acceptor.

Step (b) involves the conversion of the compound of formula III to the corresponding salt of formula IV. Step (c) involves the protection of the 6-hydroxy substituent to form the compound of formula V with the preferred protecting group being trimethylsily whereas step (d) is that wherein the metal salt of formula V is then converted to a compound of formula VII by addition of a thiocarbonyl reagent of formula VI wherein the Y leaving group is typically chloro, bromo, iodo or imidazolyl. For the purposes of this process, 1,1'-thiocarbonyldiimidazole is the preferred thiocarbonyl reagent due to its crystalline nature and ease of use.

In Step (b) typically, a polar solvent such as methanol, ethanol, dimethylformamide (DMF), tetrahydrofuran or water is utilized. Metal salts, e.g. those of silver, mercury or copper can be utilized in this step and may be any reactive salt of the metal in which the anion does not interfere in the reaction. Silver salts are preferred and include organic and inorganic salts such as silver nitrate, silver fluoborate and silver acetate, and the like with silver nitrate being most preferred. Typical suitable copper salts are those such as copper (II) acetate and copper (II) nitrate. Typical suitable mercury salts are those such as mercuric acetate. Lead salts may also be utilized although the reaction will be much slower. Silver salts are most preferred due to their ease of recovery and relative nontoxicity. The use of an acid acceptor, e.g., pyridine or triethylamine, facilitates the reaction of this step. The reaction preferably takes place under an inert atmosphere with a nitrogen atmosphere preferred.

Step (c) involves the protection of the 6-hydroxy substituent. Hydroxy protecting groups are well known in the beta lactam art. A particularly preferred reagent for this step is bis trimethyl silylacetamide which readily forms the trimethylsilyl protecting group at the 6-hydroxy moiety. Preferably step (c) is conducted directly upon the completion of step (b) without isolation of the metal salt intermediate of formula IV. Thus the inert solvent utilized, e.g. DMF, may be the same as the one used in step (b). Solvents such as chloroform, methylene chloride and the like may also be employed in step (c). Temperatures for the reaction of step (c) range from 0° C. to 30° C.

Step (d) is wherein the metal salt of formula V is converted to the thiocarbonyl compound of formula VII by reaction of the compound of formula V with the thiocarbonyl reagent of formula VI. Typically, this step (d) is conducted directly upon the completion of step (c) without isolation of the metal salt intermediate of formula V. Thus, the solvent utilized may be the same as the one used in step (c). Temperatures for the reaction of step (d) range from about 10° C.–45° C., with room temperature (about 25° C.) being generally preferred.

Step (e) involves the cyclization of the compound of formula VII into the thione of formulas VIII(a) and VIII(b). The reaction is typically conducted in an anhydrous inert organic solvent such as tetrahydrofuran and the like. An essentially equimolar amount of a strong base such as lithium diisopropyl amide (LDA), lithium di(trimethylsily)amine and the like is added to the system to effect cyclization. Typically, the reaction is conducted at from −50° to −100° C. and preferably at −70° C. and is generally complete from within 5 minutes to 24 hours.

Step (f) involves the removal of the 6-hydroxy protecting group in the compound of formulas VIII(a) and VIII(b) to form the compound of formulas IX(a) and IX(b).

Methods for the removal of this group are well known in the β-lactam art. Preferably, when the 6-hydroxy protecting group is trimethylsilyl, addition of a mild aqueous acid solution, such as acetic acid, to the same solution as is employed in step (e) effects removal.

The term "removable hydroxy protecting group" as used herein means any such group conventionally used for this purpose, with the only requirement being compatibility with the hydroxy substituent on the penems and removability utilizing elemental zinc or any other conventional agent for this purpose which will not adversely affect the penem structure. For the purpose of this invention, preferred hydroxy protecting groups include trichloroethoxycarbonyl, dimethyltributylsilyl, trimethylsilyloxycarbonyl and trimethylsilyl.

Step (g), wherein the compound of formula IX(a) and IX(b) is reacted with compounds of formula X or XI, is conducted in an inert atmosphere, such as nitrogen, in an organic solvent such as tetrahydrofuran (THF). The reaction is completed within 1 to 3 hours to yield allyl-2-(heterocycloalkylthio)-6-(1-hydroxyethyl)penem-3-carboxylate.

Removal of the allyl group in Step H is effected by the addition of the above allyl ester to a solution containing palladium (zero) and an alkali alkylcarboxylate, carboxylic acid or aqueous carbonate. This is described by McCombie in U.S. Pat. No. 4,314,942 which is incorporated herein by reference. Under these conditions, the removal of the allyl group and formation of the alkali salt or the free acid of the compound occurs.

The following example illustrates the preparation of the compounds and compositions of this invention.

EXAMPLE 1

Preparation of allyl (5R,6S,8R)-2-thiol-6-(1-hydroxyethyl)penem-3-carboxylate and allyl (5R,6S,8R)-2-thiocarbonyl-6-(1-hydroxyethyl)penem-3-carboxylate (A) Preparation of (3S,4R)-1-(allyloxycarbonylmethyl)-3-(1-hydroxyethyl)-4-(triphenylmethylthio)azetidin-2-one Add 3 gm of (3S,4R)-3-(1-hydroxyethyl)-4-(triphenylmethylthio)azetidin-2-one to 10 ml of acetonitrile containing 0.286 gm of cesium carbonate. Add 0.2 gm of α-iodo allyl acetate to the system. Stir the system at room temperature for 16 hours. Dilute with ether (50 ml), filter and wash the ether layer with 1% aqueous phosphoric acid, followed by water. After drying over sodium sulfate remove solvent to give a foamy solid.

NMR: δ=8,4 1H, s; 7.65, 1H, d (J=1 Hz); 7.05, 1H (dJ=1 Hz); 5.95, 1H, d (J=2 Hz); 5.8, 1H, m; 5.45-5.1, 2H, m; 4.3, 1H, m; 4.1, 2H, Q (J=16 Hz); 3.5, d d (J=2,6); 1.35; 3H; d (J=6 Hz).

(B) Preparation of Silver (3S,4R)-3-(1-hydroxyethyl)-1-allylcarbonylmethylazetidin-2-one-4-thiolate To a 50 ml flask equipped with a nitrogen atmosphere add 10 ml of methanol and 460 mg of (3s,4R)-1-(allyloxycarbonylmethyl)-3-(1-hydroxyethyl)-4-triphenylmethylthio)azetidin-2-one. To this system add 160 mg silver nitrate and 0.15 ml of pyridine. Stir the system at 20° C. for 1 hour. Stop the reaction and remove the methanol by stripping to give the title compound.

(C) Preparation of Silver (3S,4R)-3-(1-trimethylsilyloxy)ethyl)-1-allyloxycarbonylmethylazetidin-2-one-4-thiolate Add the entire amount of silver (3S,4R)-3-(1-hydroxyethyl)-1-allyloxycarbonylmethylazetidin-2-one-4-thiolate produced in step (B) above to 25 ml of methylene chloride. To this system add 1.1 ml of bis trimethyl silylacetamide. Stir the system at room temperature for 15 minutes to give the title compound.

(D) Preparation of (3S,4R)-1-(allyloxycarbonylmethyl)-3-(1-trimethylsilyloxyethyl)-4-(1-imidazolylthiocarbonylthio)azetidin-2-one After completion of step (C) above and to the same solution add 350 mg of thiocarbonyldiimidazole. Stir the system at room temperature for 3 hours. Filter the solution and wash the precipitate with methylene chloride. Collect the filtrate and remove the methylene chloride by stripping. Chromatograph the residue on silica gel eluting with 20% ethyl acetate/methylene chloride to yield 335 mg of the title compound.

(E) Preparation of (5R,6S,8R) allyl-2-thiol-6-(1-trimethylsilyloxyethyl)penem-3-carboxylate and (5R,6S,8R) allyl-2-thiocarbonyl-6-(1-trimethylsilyloxyethyl)penam Add 170 mg of (3S,4R)-1-(allyloxycarbonylmethyl)-3-(1-trimethylsilyloxyethyl)-4-(1-imidazolythiocarbonylthio)azetidin-2-one to 40 ml of anhydrous tetrahydrofuran under a nitrogen atmosphere. Cool the system to −78° C. and then add 0.6 ml of 1M lithium di-(trimethylsilyl) amine in hexane dropwise to the system. Stir the system at −78° C. for 5 minutes. Add 0.2 ml of acetic acid to the system. Diluting the system to 200 ml with methylene chloride. Wash the organic solution with water, aqueous sodium bicarbonate solution and again with water. Purify the product by chromatography by rapidly eluting the sample through silica gel with 5% ethyl acetate/methylene chloride to afford 125 mg of the desired products and the desilylated products.

(F) Preparation of (5R,6S,8R) Allyl-2-thiol-6-(1-hydroxyethyl)penem-3-carboxylate and (5R,6S,8R) Allyl-2-thiocarbonyl-6-(1-hydroxyethyl)penam To a 25 ml flask add the entire mixture produced in Step (E) along with 5 ml of tetrahydrofuran, 1 ml of water and 1 ml of acetic acid. Stir the system at room temperature for 2 hours. Add ethyl acetate to the solution and wash the organic phase with sodium bicarbonate solution, water and then brine. Dry the organic phase over anhydrous sodium sulfate, filter and remove the solvent by stripping to give the title compound.

EXAMPLE 2

(5R,6S,8R)-2-[2-(N-piperazinyl)ethylthio]-6-(1-hydroxyethyl)penem-3-carboxylic acid (A) Preparation of 1-Hydroxyethyl-4-allyloxycarbony piperazine Stir 5 g of N-β-hydroxyethylpiperazine, 7.5 g allylchloroformate and 12 g potassium carbonate in 100 ml water at 0° C. for 1 hour. Extract the resultant mixture with ethyl acetate and evaporate the solvent to give the title compound.

(B) Preparation of 1-Allyloxycarbonyl-4-trifluoromethane sulfonylethyl piperazine Dissolve 1 g of the product of Step A in 10 ml methylene chloride and cool to −20° C. Add 0.78 ml trifluoromethanesulfonic anhydride and let stand 1 hour to obtain the title compound.

(C) Preparation of Allyl (5R,6S,8R)-2-[2-(N-Piperazinyl)Ethylthio]-6-(1-Hydroxyethyl)Penem-3-Carboxylate Dissolve 600 ml of the product of Example 1 in 25 ml tetrahydrofuran and add 700 mg sodium bicarbonate in 10 ml water. Slowly add the solution prepared in Step B until TLC shows no starting material remaining. Evaporate the organic layer and purify the resultant residue by column chromatography (silica gel eluted with methylene chloride changing to ethyl acetate) to obtain the title compound.

(D) Preparation of (5R,6S,8R)-2-[2-(N-Piperazinyl)Ethylthio]-6-(1-Hydroxyethyl)Penem-3-Carboxylic Acid Dissolve 570 mg of the product of Step C in 10 ml acetonitrile and 10 ml methylene chloride. Add 0.80 ml 2-ethylhexanoic acid, 0.3 ml pyridine, 500 mg triphenylphosphine and 100 mg Pd° reagent in 2 ml methylene chloride. After 2 hours, evaporate the solvent in vacuo and partition the resultant residue in water/methylene chloride. Purify the aqueous layer by high pressure liquid chromatography using a Whatman OD53 M9 column and eluting with 3% acetonitrile in water to obtain the title compound:

NMR-90 mHz—δ=1.3 (D,J=6 Hz, 3p), 2.7-3.5 (m, 12P), 3.80 (DD,J=6 Hz, 1p), 4.3 (m, 1P), 5.7 (D,J=1 Hz, 1P).

By following the procedures outlined in the above examples, the following compounds of this invention may be prepared:

Compounds of the formula

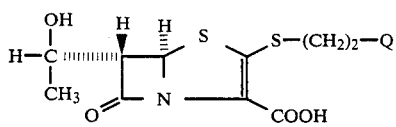

wherein Q is

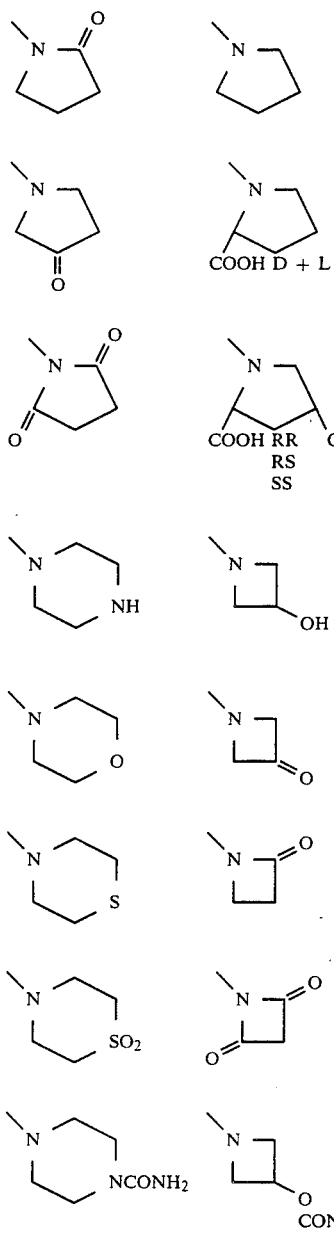

Compounds of the formula

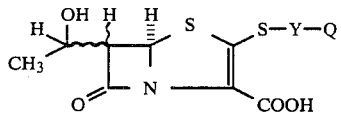

wherein Q is as defined above and Y is

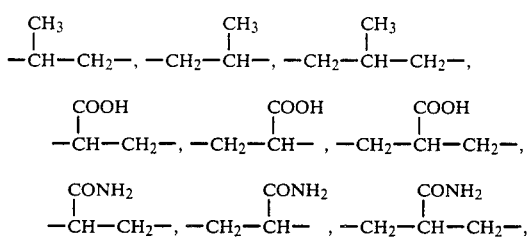

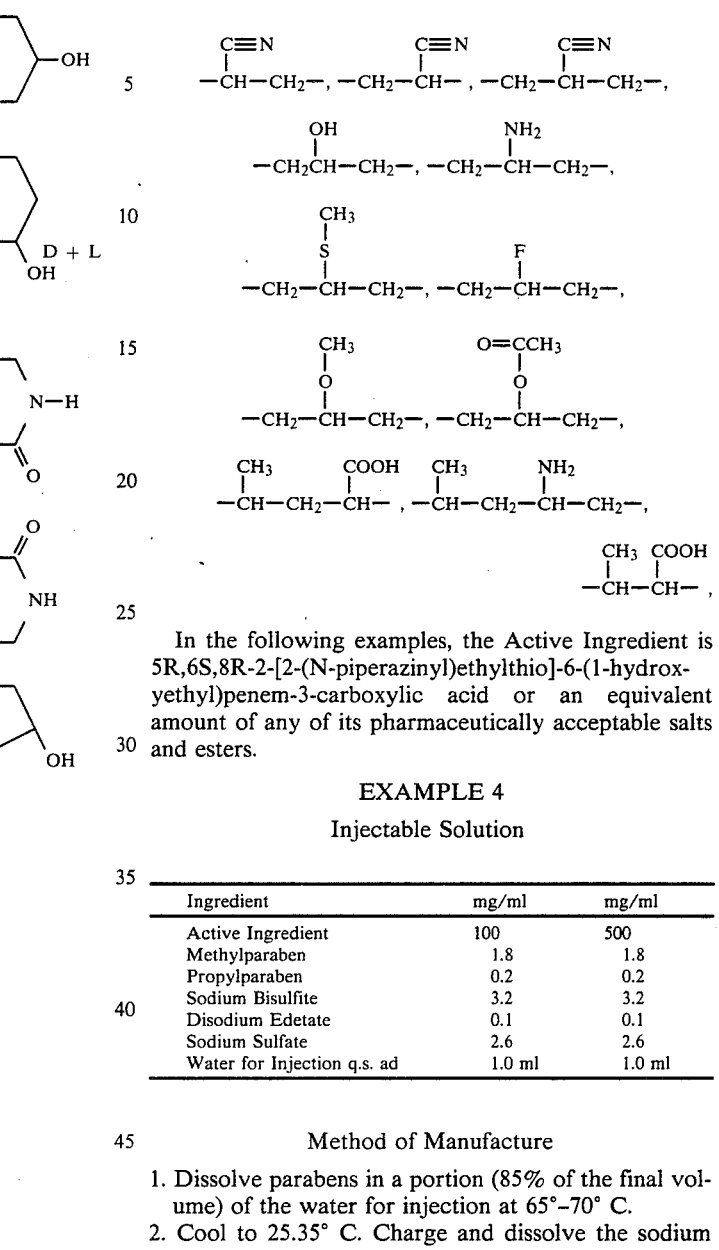

In the following examples, the Active Ingredient is 5R,6S,8R-2-[2-(N-piperazinyl)ethylthio]-6-(1-hydroxyethyl)penem-3-carboxylic acid or an equivalent amount of any of its pharmaceutically acceptable salts and esters.

EXAMPLE 4

Injectable Solution

| Ingredient | mg/ml | mg/ml |
|---|---|---|
| Active Ingredient | 100 | 500 |
| Methylparaben | 1.8 | 1.8 |
| Propylparaben | 0.2 | 0.2 |
| Sodium Bisulfite | 3.2 | 3.2 |
| Disodium Edetate | 0.1 | 0.1 |
| Sodium Sulfate | 2.6 | 2.6 |
| Water for Injection q.s. ad | 1.0 ml | 1.0 ml |

Method of Manufacture

1. Dissolve parabens in a portion (85% of the final volume) of the water for injection at 65°–70° C.
2. Cool to 25.35° C. Charge and dissolve the sodium bisulfite, disodium edetate and sodium sulfate.
3. Charge and dissolve the active ingredient.
4. Bring the solution to final volume by adding water for injection.
5. Filter the solution through 0.22μ membrane and fill into appropriate containers.
6. Terminally sterilize the units by autoclaving.

EXAMPLE 5

Injectable Powder: (per vial)

| | g/vial | g/vial |
|---|---|---|
| Active Ingredient | 0.5 | 1.0 |

Add sterile water for injection or bacteriostatic water for injection for reconstitution.

We claim:

1. Compounds represented by the formula

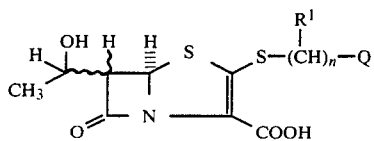

wherein
Q is

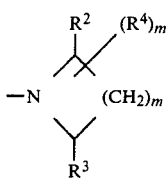

R$^1$ is hydrogen, lower alkyl, carboxy, carbamyl, cyano, hydroxy, amino, lower alkylthio, fluoro, lower alkoxy, or lower alkanoyloxy, provided that when R$^1$ is attached to a carbon atom adjacent to S or N, R$^1$ is not hydroxy, amino, lower alkylthio, fluoro, lower alkoxy, or lower alkanoyloxy;

R$^2$ and R$^3$ are independently selected from hydrogen, lower alkyl, amino(lower)alkyl, mono- and di-(lower)alkylamino(lower)alkyl, carboxy(lower)alkyl, carboxy, hydroxy(lower)alkyl, cyano, oxo, carbamyl, and mono- or di-(lower)alkylcarbamyl;

R$^4$ is R$^2$, sulfo(lower)alkyl, hydroxy, amino, mono- and di-(lower)alkylamino, (lower)alkylsulfonate, sulfamyl, halogeno, hydroxylimino, or lower alkoxyimino;

m and n are 1 to 4; and the pharmaceutically acceptable salts and esters thereof, in racemic or optically active form.

2. Compounds of claim 1 wherein n is 2 to 4.
3. Compounds of claim 1 wherein n is 2.
4. Compounds of claim 1 wherein R$^2$ and R$^3$ are independently selected from hydrogen and oxo.
5. Compounds of claim 1 wherein R$^4$ is selected from the group consisting of amino, hydroxy, oxo and carboxy.
6. Compounds of claim 1 wherein m is 2 or 3.
7. Compounds of claim 1 wherein p is 1.
8. A compound of claim 1 which is 5R,6S,8R-2-[2-(1-pyrrolidinyl)ethylthio]-6-(1-hydroxyethyl)-penem-3-carboxylic acid.
9. A pharmaceutical composition comprising an antibacterial effective amount of a compound of claim 1 in admixture with a pharmaceutically acceptable carrier therefor.
10. A method of preventing bacterial infections in warm blooded animals in need of such treatment which comprise administering an antibacterial effective amount of a compound of claim 1.
11. A composition according to claim 10 adapted for parenteral administration.
12. Compounds represented by the formula

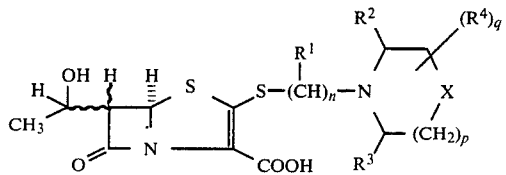

wherein
R$^1$ is hydrogen, lower alkyl, carboxy, carbamyl, cyano, hydroxy, amino, lower alkylthio, fluoro, lower alkoxy, or lower alkanoyloxy, provided that when R$^1$ is attached to a carbon atom adjacent to S or N, R$^1$ is not hydroxy, amino, lower alkylthio, fluoro, lower alkoxy, or lower alkanoyloxy;

R$^2$ and R$^3$ are independently selected from hydrogen, lower alkyl, amino(lower)alkyl, mono- and di-(lower)alkylamino(lower)alkyl, carboxy(lower)alkyl, carboxy, hydroxy(lower)alkyl, cyano, oxo, carbamyl, and mono- or di-(lower)alkylcarbamyl;

R$^4$ is R$^2$, sulfo(lower)alkyl, hydroxy, amino, mono- and di-(lower)alkylamino, (lower)alkylsulfonate, sulfamyl, halogeno, hydroxylimino, or lower alkoxyimino;

X is O, S or SO$_2$;
n is 1 to 4;
p is 1 or 2;
q is 1 to 3; and the pharmaceutically acceptable salts and esters thereof, in racemic or optically active form.

13. Compounds of claim 12 wherein n is 2 to 4.
14. Compounds of claim 12 wherein n is 2.
15. Compounds of claim 12 wherein R$^2$ and R$^3$ are independently selected from hydrogen and oxo.
16. Compounds of claim 12 wherein R$^4$ is selected from the group consisting of amino, hydroxy, oxo and carboxy.
17. Compounds of claim 12 wherein p is 1.
18. A pharmaceutical composition comprising an antibacterial effective amount of a compound of claim 12 in admixture with a pharmaceutically acceptable carrier therefor.
19. A method of preventing bacterial infections in warm blooded animals in need of such treatment which comprises administering an antibacterial effective amount of a compound of claim 13.
20. Compounds represented by the formula

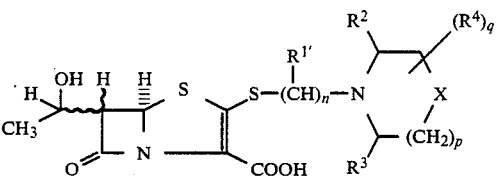

wherein
R$^{1'}$ is carboxy, carbamyl, cyano, hydroxy, amino, lower alkylthio, fluoro, lower alkoxy, or lower alkanoyloxy, provided that when R$^{1'}$ is attached to a carbon atom adjacent to S or N, R$^{1'}$ is not hydroxy, amino, lower alkylthio, fluoro, lower alkoxy, or lower alkanoyloxy;

R$^2$ and R$^3$ are independently selected from hydrogen, lower alkyl, amino(lower)alkyl, mono- and di-(lower)alkylamino(lower)alkyl, carboxy(lower)alkyl, carboxy, hydroxy(lower)alkyl, cyano, oxo, carbamyl, and mono- or di-(lower)alkylcarbamyl;

$R^4$ is $R^2$, sulfo(lower)alkyl, hydroxy, amino, mono- and di-(lower)alkylamino, (lower)alkylsulfonate, sulfamyl, halogeno, hydroxylimino, or lower alkoxyimino;

X is NH, $NR^2$ or $NCOR^2$;

n is 1 to 4;

p is 1 or 2;

q is 1 to 3; and the pharmaceutically acceptable salts and esters thereof, in racemic or optically active form.

21. Compounds of claim 20 wherein n is 2 to 4.

22. Compounds of claim 20 wherein n is 2.

23. Compounds of claim 20 wherein $R^2$ and $R^3$ are independently selected from hydrogen and oxo.

24. Compounds of claim 20 wherein $R^4$ is selected from the group consisting of amino, hydroxy, oxo and carboxy.

25. Compounds of claim 20 wherein p is 1.

26. A pharmaceutical composition comprising an antibacterial effective amount of a compound of claim 20 in admixture with a pharmaceutically acceptable carrier therefor.

27. A method of preventing bacterial infections in warm blooded animals in need of such treatment which comprises administering an antibacterial effective amount of a compound of claim 20.

* * * * *